United States Patent
Shibata

(10) Patent No.: US 7,628,922 B2
(45) Date of Patent: Dec. 8, 2009

(54) PREANALYSIS TREATMENT METHOD AND APPARATUS FOR ANALYSIS OF POLYCYCLIC AROMATIC HYDROCARBONS

(75) Inventor: Keiko Shibata, Kanagawa (JP)

(73) Assignee: Isuzu Motors Limited, Tokyo (JP)

( * ) Notice: Subject to any disclaimer, the term of this patent is extended or adjusted under 35 U.S.C. 154(b) by 347 days.

(21) Appl. No.: 10/578,845

(22) PCT Filed: Feb. 17, 2005

(86) PCT No.: PCT/JP2005/002401

§ 371 (c)(1),
(2), (4) Date: May 10, 2006

(87) PCT Pub. No.: WO2005/093407

PCT Pub. Date: Oct. 6, 2005

(65) Prior Publication Data

US 2007/0138097 A1   Jun. 21, 2007

(30) Foreign Application Priority Data

Mar. 26, 2004   (JP) .............................. 2004-090879

(51) Int. Cl.
*B01D 15/08* (2006.01)
(52) U.S. Cl. ................................... 210/656; 210/198.2
(58) Field of Classification Search ................ 210/656, 210/635, 659, 198.2; 436/161, 178; 585/828, 585/830
See application file for complete search history.

(56) References Cited

U.S. PATENT DOCUMENTS 5,076,909 A  * 12/1991  Overfield et al. ............ 208/177
5,080,798 A  *  1/1992  James ......................... 210/656
2003/0027354 A1  2/2003  Geli

FOREIGN PATENT DOCUMENTS

| EP | 0400989 | 12/1990 |
|----|---------|---------|
| EP | 1266686 | 12/2002 |
| FR | 2825649 | 12/2002 |
| JP | 56-089058 | * 7/1981 |
| JP | 06-094697 | 4/1994 |

(Continued)

OTHER PUBLICATIONS

PTO Translation No. 08-6627 of Matsushita (Japan Patent No. 56-089058).*

(Continued)

*Primary Examiner*—Ernest G Therkorn
(74) *Attorney, Agent, or Firm*—Antonelli, Terry, Stout & Kraus, LLP.

(57) ABSTRACT

The present invention provides a preanalysis treatment method for nitropolycyclic aromatic hydrocarbons present in diesel engine exhaust particulates and the like. The method comprises feeding a test solution 160 in which a sample containing polycyclic aromatic hydrocarbons is dissolved in a solvent to a silica gel column 170 using an eluent lowest in polarity among a plurality of eluents 110, 120 and 130 to be a mobile phase for the test solution unlike the solvent and to differ in polarity from each other; and then allowing polar solvents to flow in ascending order of polarity to fractionate nitropolycyclic aromatic hydrocarbons and polycyclic aromatic hydrocarbons other than the nitropolycyclic aromatic hydrocarbons.

4 Claims, 2 Drawing Sheets

FOREIGN PATENT DOCUMENTS

| | | | |
|---|---|---|---|
| JP | 6-94697 | * | 4/1994 |
| JP | 11-304782 | | 11/1999 |
| JP | 2000-249633 | | 9/2000 |
| JP | 2001-021497 | | 1/2001 |
| JP | 2005-037287 | | 2/2005 |
| WO | WO 01/46687 | | 6/2001 |

OTHER PUBLICATIONS

PTO Translation No. 08-6644 of Takamura (Japan Patent No. 6-94697).*
Snyder (Introduction to Modern Liquid Chromatography, John Wiley &Sons, Inc., New York, 1979, pp. 662-686.*
Machine Translation of Japan 11-304782.*
PTO Translation No. 08-6619 of Kokai 2000-249633.*
PTO Translation No. 08-6618 of Kokai 13021487.*
Translation of the International Preliminary Report on Patentability, for Application No. PCT/JP2005/002401, dated Dec. 7, 2006.
Japanese Official Action dated Apr. 1, 2008, for Application No. JP 2004-090879.
L. Peschke, et al., "Improved analysis of polycyclic aromatic hydrocarbons in aqueous solutions by gas chromatography", Fresenius' Journal of Analytical Chemistry, (1995) vol. 351, pp. 622-624.
P. Fernandez, et al., "Use of off-line gel permeation chromatography-normal-phase liquid chromatography for the determination of polycyclic aromatic compounds in environmental samples and standard reference materials (air particulate mater and marine sediment)", *Journal of Chromatography*, vol. 625, pp. 141-149.
Supplementary European Search Report dated Feb. 13, 2009, for Application No. EP 05 71 9203.

* cited by examiner

PREANALYSIS TREATMENT METHOD AND APPARATUS FOR ANALYSIS OF POLYCYCLIC AROMATIC HYDROCARBONS

REFERENCE TO RELATED APPLICATIONS

This application is a 371 of PCT/JP05/02401 filed Feb. 17, 2005

TECHNICAL FIELD

The present invention relates to a preanalysis sample treatment method and a preanalysis sample treatment apparatus suitable for analysis of polycyclic aromatic hydrocarbons occurring in exhaust gas microparticulates contained in the atmosphere or in engine exhaust gas, in particular, a preanalysis treatment method and a preanalysis treatment apparatus, suitable for fractionation of nitropolycyclic aromatic hydrocarbons and polycyclic aromatic hydrocarbons other than the nitropolycyclic aromatic hydrocarbons from diesel particulates contained in diesel engine exhaust gas, and quantitatively analyzing the nitropolycyclic aromatic hydrocarbons and the polycyclic aromatic hydrocarbons other than the nitropolycyclic aromatic hydrocarbons, respectively.

BACKGROUND ART

Diesel particulates contained in diesel engine exhaust gas are formed by condensation and agglomeration of unburned components of fuel and lubricating oil, and are agglomerates in which an organic solvent-soluble organosoluble fraction (hereinafter, abbreviated as SOF) and an organic solvent-insoluble fraction (hereinafter, abbreviated as ISOF) including sulfate, nitrates, elemental carbon and metals are mixed together in a complex manner. The composition of such particulates is known to be affected strongly by various factors such as fuel, lubricating oil, engine type and operation conditions. The polycyclic aromatic hydrocarbons and the nitropolycyclic aromatic hydrocarbons are contained in the SOF of diesel particulates, and although the contents thereof are extremely small, the methods for analyzing the hydrocarbons have been recently investigated because of their high carcinogenicity (see, for example, Patent Documents 1 and 2). Because the contents of these substances are small, these substances cannot be detected unless a large number of interfering substances are eliminated to enhance the analytical sensitivity and precision. For that purpose, the sample is required to be subjected to a preanalysis treatment to eliminate interfering components in such a way that the sample adapts to the targets to be analyzed.

Patent Document 1: Japanese patent Application No. 2003-275806
Patent Document 2: Japanese Patent Laid-Open No. 2001-21497

DISCLOSURE OF THE INVENTION

Patent Documents 1 and 2 disclose a quantitative analysis of the polycyclic aromatic hydrocarbon in a fluorescence detection mode and that in a chemiluminescence mode, respectively. In any one of these analyses, interfering substances are eliminated and a pretreatment to enhance the analytical sensitivity and precision is applied before polycyclic aromatic hydrocarbons are quantitatively analyzed. The pretreatment method for analysis of diesel particulates collected from exhaust is generally needed to be a pretreatment method including at least four steps, as shown in FIG. 2.

A first step of extraction is a step of extracting with an organic solvent the SOF from the diesel particulates, for which a method called the Soxhlet extraction method or the ultrasonic extraction method is commonly used. Any one of these methods has advantages and disadvantages; the supersonic extraction method that is convenient is familiar in universities and national research institutes. In the present invention, the Soxhlet extraction method that achieves a high recovery ratio is used.

A second step of concentration/evaporation-to-dryness is a step of performing concentration to improve the analytical sensitivity and for performing evaporation-to-dryness to evaporate the organic solvent, for which a concentration/evaporation-to-dryness apparatus, called Kuderna-Danish concentrator, using nitrogen gas under atmospheric pressure or a reduced pressure type concentration/evaporation-to-dryness apparatus capable of recovering the organic solvent used for extraction without releasing it into the atmosphere is used.

A third step of purification is a step of fractionating nitropolycyclic aromatic hydrocarbons or polycyclic aromatic hydrocarbons other than the nitropolycyclic aromatic hydrocarbons, for which the liquid-liquid partition method, column chromatography method or solid phase extraction method is commonly used.

A fourth step of concentration/evaporation-to-dryness/solvent-replacement is a step of concentration to improve analytical sensitivity, drying to evaporate the organic solvent and dissolving the solid product into an eluent for feeding into an analytical apparatus, wherein concentration/evaporation-to-dryness is performed by using the same apparatus as in the second step.

However, even when anyone of the liquid-liquid partition method, the column chromatography method and the solid phase extraction method is applied, a large number of steps are required and a long operation time is also required, and consequently, it is highly probable that fractionated substances are lost or decomposed; and there are also problems including a reproducibility problem such that the elimination and extraction of the interfering substances vary depending on the operators in charge, so that it has been very difficult to prepare appropriate samples well adapted to the targets to be analyzed.

For example, the liquid-liquid partition method is a method in which two solvents different in the solubility for the target component are used and the components other than the target component are transferred into one of the solvents so as to extract only the target component; however, there are a problem of emulsion formation, and a reproducibility problem because the separation operation is complex and requires a long period of time, and also requires a skill.

The column chromatography method is a method in which the target component is taken out by taking advantage of the difference in elution time due to the retention/nonretention effect between the sample in the eluent and the chromatography packing packed in the preparative column; however, this method is low in recovery ratio for a large amount of solvent to be used and there is also a reproducibility problem associated with this low recovery ratio. There is also a method in which nitropolycyclic aromatic hydrocarbons are set as the target components, only the polycyclic aromatic hydrocarbons other than the nitropolycyclic aromatic hydrocarbons are eliminated from the SOF (see, for example, Patent Document 2); however, there is a problem such that if interfering substances similar in behavior to the nitropolycyclic aromatic hydrocarbons are contained, these interfering substances are also extracted.

The solid phase extraction method is a method in which the target components are taken out by use of a solid phase extraction cartridge; however, because a plurality of solid phase extraction cartridges are used to take out the target components, replacement operation of the solid phase extraction cartridge and the tray is required every time when each of the cartridges is used, the extraction of the target components is significantly affected by the flow rate, leading to a reproducibility problem.

For the purpose of solving the aforementioned problems, the present invention adopts in the purification step a technique utilizing the van der Waals force between the sample in the eluent for pretreatment and the packing for normal phase chromatography, and consequently the present invention can provide a preanalysis treatment method and a preanalysis treatment apparatus to efficiently separate the nitropolycyclic aromatic hydrocarbons, the polycyclic aromatic hydrocarbons other than the nitropolycyclic aromatic hydrocarbons and the interfering substances from the SOF.

As described above, the present invention has an advantageous effect to efficiently separate the nitropolycyclic aromatic hydrocarbons, the polycyclic aromatic hydrocarbons other than the nitropolycyclic aromatic hydrocarbons and the interfering substances from the SOF.

DESCRIPTION OF REFERENCE NUMERALS

100 Chromatograph
110 n-Hexane
120 Dichloromethane
130 Acetonitrile
140 Gradient mixer
150 Pump
160 Injector
170 Silica gel column
180 Fraction collector
300 Controller

BEST MODE FOR CARRYING OUT THE INVENTION

Figure 1:
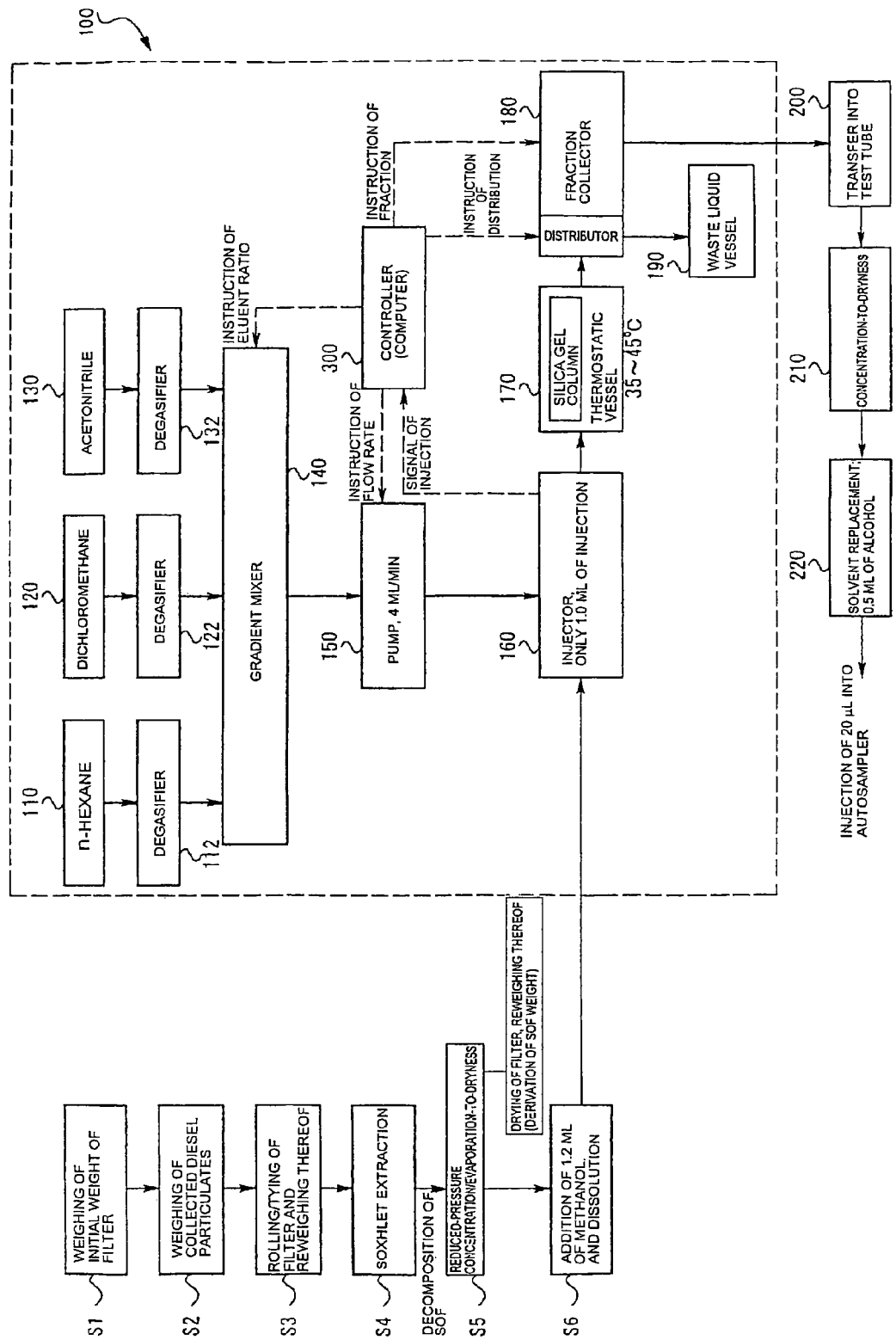
FIG. 1 is a block diagram illustrating the pretreatment method and the apparatus thereof of the present invention.
Figure 2:
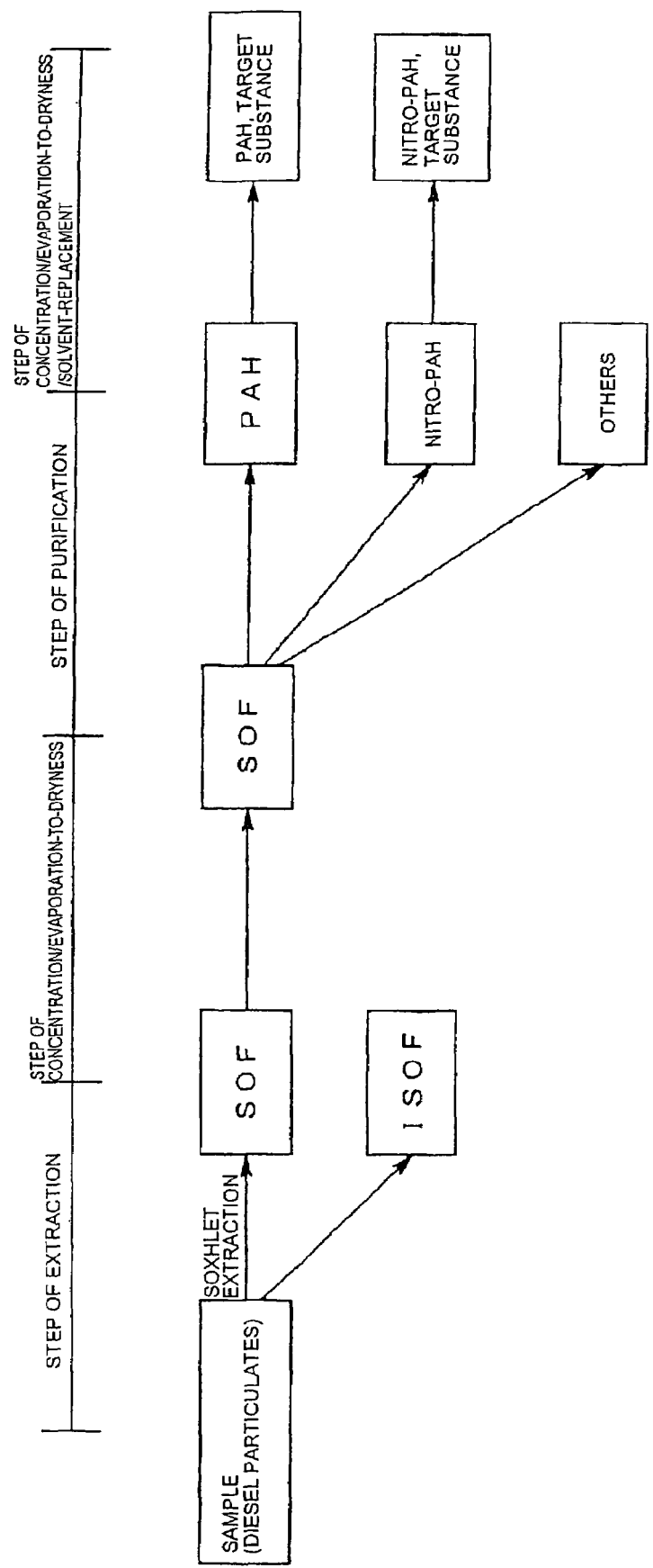
FIG. 2 is a schematic diagram illustrating the steps in the pretreatment method.

FIG. 1 is a diagram illustrating an example of a preanalysis treatment apparatus for nitropolycyclic aromatic hydrocarbons contained in the atmosphere or in diesel particulates and a pretreatment method according to the present invention.

A sample of the nitropolycyclic aromatic hydrocarbons, as the targets of analysis, contained in the atmosphere or in diesel particulates is prepared through the treatment steps to be described below.

In step S1, initial weighing of, for example, a Teflon (trademark) coating fiber filter of 70 mm in diameter is carried out.

Next, in step S2, atmospheric particulates or diesel particulates are collected on the filter by means of a collector, the filter is placed at least 2 hours or more in a thermostatic room at 25° C. with a humidity of 50% RH, and thereafter the weight of the particulates is weighed.

In step S3, the filter is rolled into a size that will fit into an extraction glass vessel, to be tied with a nickel wire having been washed with acetone a few times so as not to be untied, and then the filter is reweighed.

In step S4, the Soxhlet extraction with dichloromethane, an organic solvent, is carried out for 8 hours or more to separate the SOF.

In step S5, the extract is transferred into a glass tube for a concentrator, the tube is placed in a reduced-pressure solvent concentrator and the extract is evaporated to dryness to yield a solid matter over a period of about 1.5 hours. The evaporated dichloromethane is recovered (but cannot be recycled). The filter after extraction is once dried by heating, and thereafter allowed to stand in a thermostatic room for 2 hours or more, and then weighed to derive the weight of the SOF.

In step S6, 1.2 mL of high-performance liquid chromatography-grade (low in impurities) methanol solvent is added to the solid matter, the solid matter is dissolved, and then the solid matter is completely dissolved to give a solution by means of a supersonic generator or such.

Of the 1.2 mL of the solution, only 1.0 mL of the solution is measured off by means of a microsyringe, and is injected from an injector 160 into a high-performance liquid chromatograph that is a preanalysis treatment apparatus.

The high-performance chromatograph 100 as a purification step consists of: eluent feeders 110, 120 and 130 for feeding an eluent; degasifiers 112, 122 and 132 for degassing the respective eluents; a gradient mixer 140 for mixing the respective eluents in a predetermined ratio therebetween; a pump 150 for pressure feeding the eluent; an injector 160 for injecting the SOF as a sample; a silica gel column kept warm at 35 to 45° C. by a thermostatic vessel 170; a fraction collector 180, with a function of waste liquid disposal, for disposing of unwanted substances and fractionating the extraction target substances; and a controller 300 with a built-in computer. The controller 300 controls the eluent ratio in the gradient mixer 140, the flow rate in the pump 150, and the distribution and fractions in the fraction collector 180.

The high-performance liquid chromatograph 100 is stabilized beforehand as follows: the chromatograph is started up 2 hours in advance of injection; the solvent lines, for n-hexane 110, dichloromethane 120 and acetonitrile 130 are degassed by means of the degasifiers 112, 122 and 132, respectively; each of the lines is made to be in a condition such that no air enters the line; and over a period of 1 hour or more, n-hexane is made to flow. The respective eluents are mixed together in the gradient mixer 140 in a predetermined ratio.

Under the condition that n-hexane 110 is being flowed at a flow rate of 4 ml/min by means of the pump 150, a sample is injected from the injector 160. With an eluent low in polarity such as n-hexane, substances high in polarity such as the nitropolycyclic hydrocarbons and the polycyclic aromatic hydrocarbons other than the nitropolycyclic aromatic hydrocarbons are retained in the silica gel column and are not eluted, but contaminants low in polarity are eluted. Consequently, the contaminants are not fractionated in the fraction collector 180, but the solution flowing out of the silica gel column is made to flow into a waste liquid vessel 190.

Next, with the flow rate still being maintained at 4 ml/min, dichloromethane 120 is gradually mixed by means of the gradient mixer. Because the polycyclic aromatic hydrocarbons other than the nitropolycyclic aromatic hydrocarbons are higher in hydrophobicity than the nitropolycyclic aromatic hydrocarbons, the polycyclic aromatic hydrocarbons are weakly retained on the silica gel column and hence start to be eluted. Consequently, by means of the faction collector 180, the polycyclic aromatic hydrocarbons other than the nitropolycyclic aromatic hydrocarbons can be fractionated.

At the time point when the concentration of dichloromethane becomes 5%, the nitropolycyclic aromatic hydrocarbons start to be eluted. Accordingly, the fraction collector 180 is set so as to fractionate the nitropolycyclic aromatic hydrocarbons, and further, the concentration of dichloromethane is increased gradually up to 100%. At the time point when the concentration of dichloromethane reaches 100%, the fractionation of the fraction collector 180 is ceased, and the eluent flow is changed so as to flow into the waste liquid vessel 190.

Next, it is preferable that acetonitrile further higher in polarity is made to flow and contaminants higher in polarity than dichloromethane is removed so that the column may be able to be used again.

The target substance collected by means of the fraction collector is transferred into a test tube 200, and concentrated and evaporated to dryness by means of a concentration/evaporation-to-dryness apparatus 210, and then dissolved in a solvent that is to replace the solvent in the target substance and to be used in an analytical apparatus; thus, the target substance is converted into an appropriate sample from which interfering components are eliminated so as to be adapted to the target to be analyzed.

INDUSTRIAL APPLICABILITY

The present invention, as described above, can be applied as a preanalysis treatment method and a preanalysis treatment apparatus, suitable for fractionation of nitropolycyclic aromatic hydrocarbons and polycyclic aromatic hydrocarbons other than the nitropolycyclic aromatic hydrocarbons from diesel particulates contained in diesel engine exhaust gas, and quantitatively analyzing the nitropolycyclic aromatic hydrocarbons and the polycyclic aromatic hydrocarbons other than the nitropolycyclic aromatic hydrocarbons, respectively.

The invention claimed is:

1. A method for fractionating polycyclic aromatic hydrocarbons using a test solution in which a sample containing polycyclic aromatic hydrocarbons is dissolved in a solvent, a plurality of eluents to be a mobile phase for the test solution and different from the solvent and different in polarity from each other, and a column packed with a packing material, wherein the method comprises:
   supplying a first eluent to the column and eluting contaminants in the test solution that are low in polarity;
   mixing gradually a second eluent which is higher in polarity than the first eluent while reducing flow of the first eluent;
   controlling an eluent ratio of the first and second eluents in a gradient mixer and distribution in a fraction collector, by a controller;
   controlling the fraction collector to fractionate eluted solution by the controller, when controlling the eluent ratio of the second eluent and the first eluent in the gradient mixer to a predetermined ratio; and
   separating the polycyclic aromatic hydrocarbons.

2. The method for fractionating polycyclic aromatic hydrocarbons according to claim 1, characterized in that the solvent in which the sample is dissolved is an alcohol; one of the plurality of eluents comprises dichloromethane; and an eluent lower in polarity than dichloromethane comprises any one of n-hexane, carbon tetrachloride and toluene.

3. The method for fractionating polycyclic aromatic hydrocarbons according to claim 1, characterized in that the column is a silica gel column.

4. The method for fractionating polycyclic aromatic hydrocarbons according to claim 2, characterized in that the column is a silica gel column.

\* \* \* \* \*